(12) United States Patent
Childers et al.

(10) Patent No.: US 8,056,556 B2
(45) Date of Patent: Nov. 15, 2011

(54) INHALER NOZZLE MAINTENANCE APPARATUS AND METHOD

(75) Inventors: Winthrop D. Childers, San Diego, CA (US); Douglas A. Sexton, La Jolla, CA (US); David Tyvoll, La Jolla, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 2236 days.

(21) Appl. No.: 10/823,475

(22) Filed: Apr. 12, 2004

(65) Prior Publication Data

US 2005/0224075 A1  Oct. 13, 2005

(51) Int. Cl.
*A61M 11/00* (2006.01)
*A61M 15/00* (2006.01)
*A61M 16/00* (2006.01)
*F16K 31/02* (2006.01)
*B05B 1/08* (2006.01)
*B05B 17/04* (2006.01)
*G01D 15/16* (2006.01)
*G01D 15/02* (2006.01)

(52) U.S. Cl. ......... 128/200.14; 128/200.16; 128/200.23; 128/203.12; 128/203.15; 128/204.23; 239/102.1; 239/102.2; 239/4; 346/140.1; 346/141

(58) Field of Classification Search ............. 128/200.14, 128/200.16, 200.23, 203.12, 203.15, 204.23; 239/102.1, 102.2, 4; 346/140.1, 141
See application file for complete search history.

(56) References Cited

U.S. PATENT DOCUMENTS

| | | | | |
|---|---|---|---|---|
| 5,522,385 | A * | 6/1996 | Lloyd et al. | 128/203.26 |
| 6,158,431 | A * | 12/2000 | Poole | 128/203.12 |
| 6,302,331 | B1 | 10/2001 | Dvorsky | |
| 6,390,453 | B1 | 5/2002 | Frederickson | |
| 7,146,977 | B2 * | 12/2006 | Beavis et al. | 128/203.12 |
| 2002/0092519 | A1 | 7/2002 | Davis | |
| 2003/0081072 | A1 | 5/2003 | Trueba | |
| 2004/0195352 | A1 * | 10/2004 | Koerner et al. | 239/102.1 |

FOREIGN PATENT DOCUMENTS

| | | |
|---|---|---|
| EP | 1 211 078 | 6/2002 |
| EP | 1 222 938 | 7/2002 |
| EP | 1 442 764 | 9/2003 |
| WO | WO 03/045697 | 6/2003 |
| WO | WO 2004/003384 | 1/2004 |

* cited by examiner

*Primary Examiner* — Patricia M Bianco
*Assistant Examiner* — Nihir Patel

(57) ABSTRACT

A medication dispenser includes a thermal drop generator ejector head. Medication is maintained in a pressurized container connected to a valve under the control of control electronics and to a compliant chamber. Fluid flows from the container to the chamber and to the ejector head. In a first mode the dispenser is operable to dispense aerosolized medication. In a second mode the ejector head is purged with fluid from the container to maintain the ejector head.

16 Claims, 3 Drawing Sheets

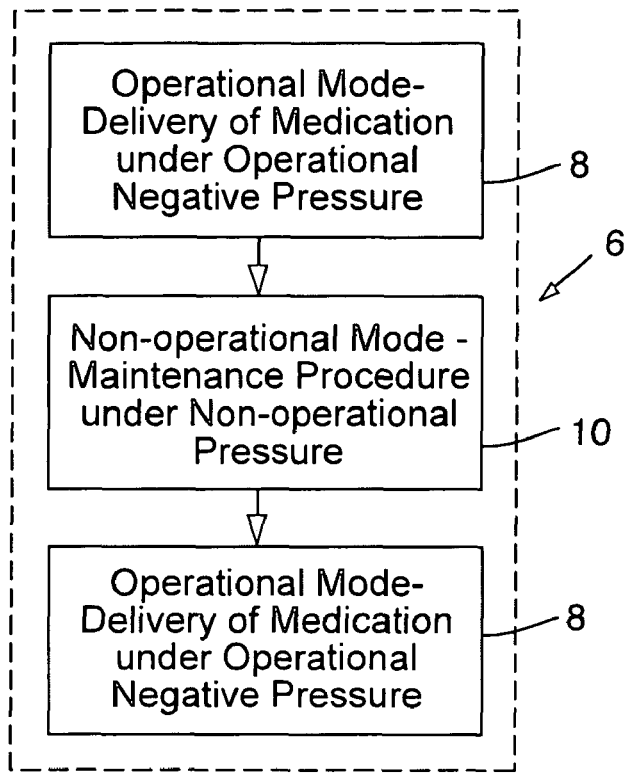
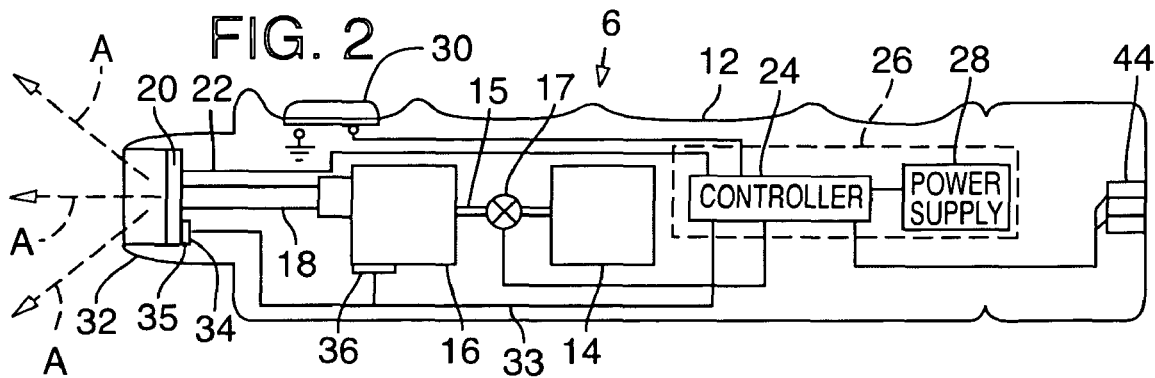
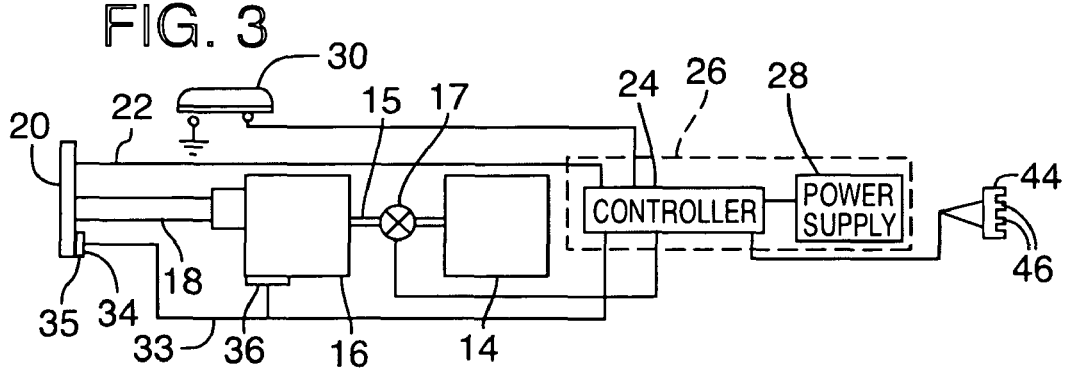

INHALER NOZZLE MAINTENANCE APPARATUS AND METHOD

TECHNICAL FIELD

This invention relates to apparatus and methods for maintenance of ejector nozzles such as thermal drop generators used in devices such as inhalers.

BACKGROUND OF THE INVENTION

Medications are often delivered to patients in the form of inhaled aerosols—gaseous suspensions of very fine liquid or solid particles in which medications are entrained. So-called pulmonary delivery of medication is in many instances a very efficient manner of delivering biological and chemical substances to the patient's bloodstream. Pulmonary delivery is especially efficient when the medication is delivered with a digitally controlled device such as a "metered dose inhaler" ("MDI") or other type of inhaler that incorporates ejector heads that are suitable for creating aerosols having very small droplet size. Such inhalers are often used to deliver asthma medications directly into a patient's lungs where the medications are rapidly absorbed into the blood stream.

As with any device intended to deliver medication to a patient, it is essential that an inhaler is maintained in proper operating condition to ensure, among other things, that the proper dosage of medication is administered to the patient, and that the device is suitably clean. However, the ejector heads that are used in digital inhalers such as MDIs can become clogged over time and repeated use. Moreover, some types of medications can accumulate on the surfaces of the ejector head. In both cases, whether one or more nozzles becomes clogged or the nozzle orifice size is reduced due to accumulated residue, the dosage of medication delivered to the patient may be affected, resulting in a lower dosage than might be needed. Clogging and accumulated residue may also impact the cleanliness of the inhaler.

There is an ongoing need to provide inhalers with smaller and very precisely controlled drop sizes. As these requirements increase, there is an ongoing need to provide such inhalers and other medication delivery apparatus having improved reliability.

BRIEF DESCRIPTION OF THE DRAWINGS

Apparatus and methods for carrying out the invention are described in detail below. Other advantages and features of the present invention will become clear upon review of the following portions of this specification and the drawings.

FIG. 1 is a flow chart setting forth the basic operational steps in accordance with an illustrated embodiment of the present invention.

FIG. 2 is a schematic side elevation view of one illustrated embodiment of the present invention as it is incorporated into a metered dose inhaler apparatus, which is one example of a medication delivery apparatus with which the invention may be used.

FIG. 3 is a schematic representation of the present invention showing an exemplary electrical circuit of the metered dose inhaler illustrated in FIG. 2.

DETAILED DESCRIPTION OF ILLUSTRATED EMBODIMENTS

Figure 4:
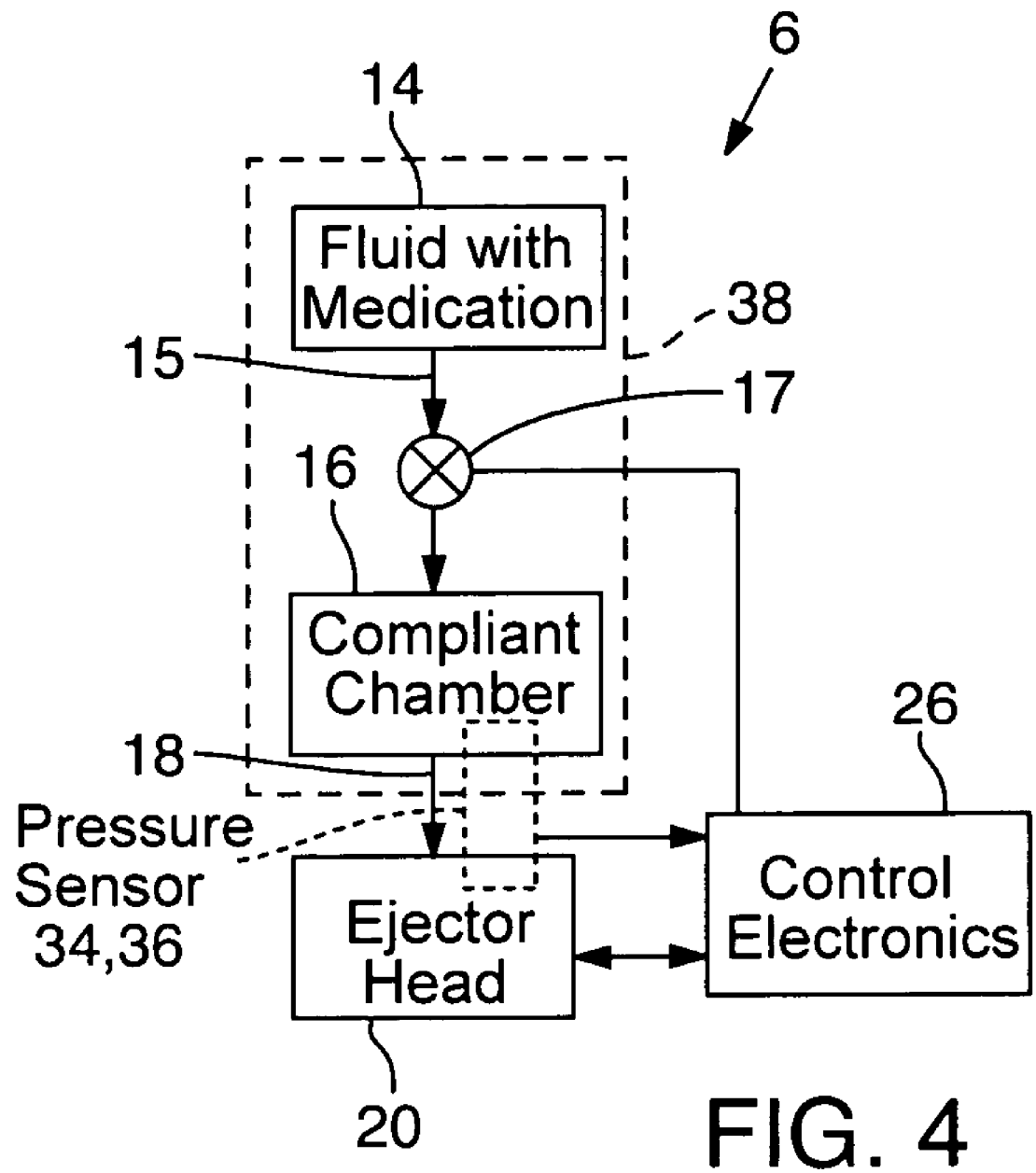
FIG. 4 is a schematic view of an illustrated embodiment of the present invention without the MDI housing shown in FIG. 2.
Figure 5:
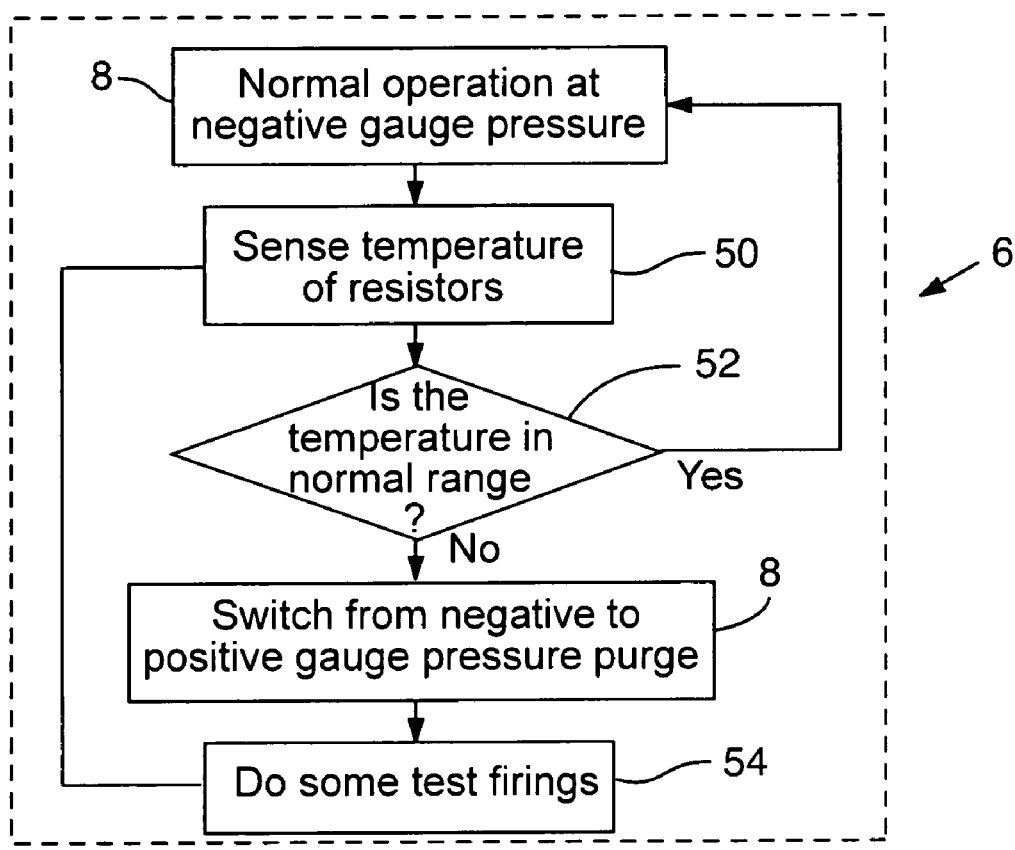
FIG. 5 is a flow chart illustrating an operational sequence included in the present invention in which a problem is detected and a maintenance mode operation is initiated

The device of the present invention is an inhalation system including an ejector head and fluid supply system coupled to a controller. The ejector head includes a plurality of individual nozzles that each ejects droplets of aerosol under the influence of the controller. The fluid supply system provides fluid to the ejector head nozzles at a pressure level that is modulated by the controller. The controller is configured to control both the operation of the ejector head nozzle ejection and the delivery of fluid to the ejector head nozzles via the fluid supply system.

The controller operates the fluid supply system to define two modes—an operating mode and a non-operating mode. During the operating mode the controller operates the ejector head to eject fluid droplets and the fluid supply system to supply fluid to the ejector head nozzles at an operating fluid supply pressure. During the non-operating or a nozzle maintenance mode the controller supplies fluid to the ejector head nozzles at a nozzle purge fluid supply pressure to allow fluid to purge air and/or blockages from the nozzles. In a preferred embodiment, the nozzle purge fluid pressure is greater than the operating fluid supply pressure.

The nozzle maintenance mode can be operable in response to a determination that the nozzles are not operating properly or it can be operable periodically. In an exemplary embodiment, the ejector includes a sensor such as a temperature sensor that is operable to determine that the nozzles are not operating properly. Upon a certain event, the sensor provides information to the controller indicative of an improper operation or a fault that triggers the controller to initiate the nozzle maintenance mode.

In an alternative embodiment, the inhalation system includes an information storage device or clock that accumulates information indicative of a time and/or number of drop ejections since a nozzle maintenance mode event. The nozzle maintenance mode may be initiated based on the accumulated time and/or number of drop ejections or usage of the inhaler since the previous nozzle maintenance mode. Of course, in yet another and perhaps most advantageous embodiment, the maintenance mode is activated or initiated based on an event or time/usage depending on what occurs first.

In an exemplary embodiment, the fluid supply system includes a reservoir system coupled to the ejector via a valve system. The controller modulates the fluid pressure at or being received by the ejector nozzles by opening and closing one or more valves of the valve system. The reservoir system includes a medicated fluid reservoir containing a supply of medicated fluid for ejection by the ejector nozzles during the operating mode. The valve system includes a valve operable by the controller that opens and closes during the operating mode to provide a stable operating fluid supply pressure by opening and closing a valve coupling between the medicated fluid reservoir and the ejector nozzles. In an exemplary embodiment, the ejector nozzles are thermal drop generator-type nozzles and the operating fluid supply pressure is a negative gauge pressure.

For background purposes, an exemplary embodiment of the drop generator ejector head comprising a thermal jet is a generally planar member having plural nozzles, each nozzle having an outlet orifice and a fluid chamber communicating with the fluid supply. The fluid chamber is a small reservoir for holding fluid prior to ejection of the fluid from the chamber through the orifice. The mechanism for ejecting the liquid from the chamber is a heat transducer proximate the fluid chamber that heats the fluid in the chamber to generate a vapor bubble in the fluid-filled chamber. Expansion of the vapor bubble in the chamber causes aerosolization of the fluid as it is ejected through the orifice. Other similar types of thermal drop generators would also suffice.

The reservoir system includes a purge reservoir containing purge fluid at a positive gauge pressure and a purge valve under control of the controller and coupling the purge reservoir to the nozzles. When a certain event or time occurs, a nozzle maintenance mode is initiated. The controller opens the purge valve coupling the positively pressurized purge reservoir to the nozzles such that purge fluid flow from the purge reservoir and out the nozzles.

In a first embodiment, the same medicated fluid reservoir and the purge reservoir are the same reservoir. In the first embodiment, the medicated fluid is utilized as purge fluid. In a second embodiment, the reservoir system includes separate reservoirs containing medicated fluid and purge fluid. In the second embodiment, there is a purge valve that is separate from the valve used for delivering medicated fluid.

FIG. 1 is a flow chart showing the basic operational modes according to the present invention. With reference to that figure, a pharmaceutical container 6, shown schematically as a block surrounding the flow chart, incorporates nozzle maintenance apparatus and methods. The nozzle maintenance apparatus according to the illustrated invention is operational in two primary modes. The first mode, or the "operational mode" is represented by block 8. The second mode, or "non-operational mode" is represented by block 10, and is also referred to herein as the nozzle maintenance mode 10.

As described in detail below, and as illustrated in FIGS. 2 and 3, pharmaceutical container 6 is exemplified in one example by a metered dose inhaler (MDI) that is operable two basic functional modalities defined above as operational mode 8 and maintenance mode 10. Operational mode 8 is the mode typically used when MDI 6 is being used to deliver medication to a patient—it is the normal operating mode for the inhaler. In this mode, the pressure in both the ejector head 20 and compliant chamber 16, which as detailed below serves as a small reservoir for the supply of medication that is to be delivered through the ejector head, is maintained at a lower pressure value (referred to herein as "negative") relative to the gauge pressure that is maintained in the supply of medication in fluid reservoir 14. The relative negative pressure in the ejector head and compliant chamber in operational mode 8 ensures stable operation of the ejector head 20, and prevents, for example, drooling of medication through the nozzles. A supply of medication is contained in reservoir 14, which may be any appropriate type of pressurizable fluid container such as a spring-loaded bag design or other type of container. The medication in reservoir 14 is typically in solution form. Fluid in reservoir 14 is maintained at an elevated pressure relative to the pressure of compliant chamber 16.

Compliant chamber 16 normally contains a desired amount of medication ready to be ejected through the ejector head 20. Medication from reservoir 14 is resupplied to compliant chamber 16 when the amount of medication in the chamber falls below a predetermined amount. When medication is to be delivered to the patient, for example when the user depresses a switch 30 on the MDI, a control system energizes resistors associated with plural nozzles (not shown) in ejector head 20, causing the resistors to heat and thereby aerosolize the medication solution. The patient inhales the droplets thus expelled.

The gauge pressure of the compliant chamber 16 is monitored and regulated closely by the control electronics. When the pressure falls outside of a predetermined normal range of operation, as for example when the supply of medication in the compliant chamber is nearly exhausted, the control electronics open the electromechanical valve to allow fluid to flow from the reservoir 14 into the compliant chamber 16. Fluid flows from the higher pressure reservoir 14 into the lower pressure compliant chamber 16 until the pressure in the chamber is within the normal range for operation, at which time the control system closes valve 17.

The second primary operational mode is maintenance mode 10. In maintenance mode 10, the control system 26 operates in response to a signal from an electronic control system to pressurize the compliant chamber and the ejector head 20 such that the pressure in these structures is positive relative to the pressure immediately outside of the ejector head. As detailed below, this reversal in pressure from the relatively lower (negative) pressure in the ejector head and compliant chamber in operational mode 8 to the relatively higher (positive) pressure in the maintenance mode 10 is preferably accomplished by pressurizing the entire fluid delivery system by opening valve 17 and disabling resistor firing. The positive pressurization state of the fluid delivery system in the maintenance mode 10 purges the nozzles of any fluid remaining thereon, and has the effect of pushing air through the nozzle, thereby cleaning them, eliminating clogs and restoring the nozzles to normal operations. Once the maintenance mode 10 is complete (as detected by tests run by control system 26, described below), the MDI 6 returns to operational mode 8.

With specific reference now to FIGS. 2 and 3, the illustrated embodiment of the inventive apparatus and methods are described herein as they are embodied in pharmaceutical container 6, which in this case is a pulmonary delivery mechanism known as a metered dose inhaler (MDI) and is at times referred to herein as MDI 6. MDIs such as the MDI 6 described herein are widely used for the delivery of aerosolized medications such as asthma medication and there are many variations of MDI delivery systems on the market. An MDI typically combines a drug with a propellant in a container that may be pressurized. The drug may be in the form of a liquid or a fine powder. Actuation of the device releases metered doses of aerosolized drug that is inhaled by the patient. The drop generator ejector head described herein may be of the type described in U.S. patent application Ser. Nos. 09/761,287 (Publication No. U.S. 2002/0092519 A1) and 10/000,425 (Publication No. 2003/0081072 A1).

It will be appreciated that the MDI 6 illustrated in FIG. 2 is intended only to illustrate one of many possible pharmaceutical containers and delivery systems that may incorporate the inventions described herein. As examples, the invention may be used with any ejection system such as piezo and other nozzle-based multiple use ejectors, and other thermal ejectors. As used herein, the term "medication" is used generally to refer to any fluid or compound, whether biological, chemical or other, delivered to a patient, whether for treatment of a medical condition or some other purpose. Other common words may be used interchangeably, such as "pharmaceutical" or "bioactive agent" and similar words.

Before turning to a detailed description of the nozzle purging apparatus and methods of the present invention, the primary components of container 6 will be described with specific reference to FIGS. 2 and 3.

Container 6 comprises an inhaler housing 12 that is configured to contain a reservoir 14 of medication, which as noted is typically provided in solution form. The medication reservoir 14 is coupled through a medication-carrying conduit 15 to a compliant chamber 16. An electromechanical valve 17 is interposed in conduit 15 between medication reservoir 14 and compliant chamber 16. Valve 17 is under the control of the control electronics, described below. Compliant chamber 16 is fluidly coupled, as for example by a needle and septum interconnection or other airflow regulator such as a thermal resistive element or piezo element, to a conduit 18 in the housing so that the medication in reservoir 14 is directed to a drop generator head, illustrated schematically at 20 (referred to as "ejector head 20"), that carries multiple drop generators comprising nozzles that are configured for generating appropriately sized aerosolized drops or particles. The drop generator head used in an MDI such as the one illustrated typically include resistor-based nozzles that eject droplets of fluid for inhalation such as those described above. It will be appreciated that the illustration of FIG. 2 is schematic, and that an MDI must necessarily be designed to have the capability for the patient to inhale a substantial volume of air in which the aerosol is entrained.

Pressure sensors 34 and 36 are provided to detect and monitor the pressure of both the ejector head 20 and the compliant chamber 16, respectively, both of which are under the control of control system 26 and which are interconnected with the control system with an appropriate flex circuit 33. Pressure sensors 34 and 36 may be of any appropriate type of sensor and may be positioned either externally to ejector head 20 and compliant chamber 16, or internally, as desired. Moreover, depending upon the structural design used in making MDI 6, a single pressure sensing unit may be configured for reading the pressure of both compliant chamber 16 and ejector head 20.

The combined components of the fluid delivery system utilized in MDI 6 are identified herein and in the drawings with reference number 38 (see, e.g., FIG. 4). Fluid delivery system 38 includes medication reservoir 14, compliant chamber 16, conduits 15 and 18 and electromechanical valve 17 and ejector head 20.

The drop generator or ejector head 20 is electrically interconnected to a controller, shown schematically at 24, which is part of the MDI electronics control system 26, for example with a flex circuit 22. Among other functions described below, controller 24 generates and sends suitably conditioned control signals to drop generator head 20 to initiate delivery of the medication to the patient by firing the nozzles contained in the ejector head. The MDI control system 26 includes controller 24, a power supply 28 and operator switch 30. The controller 24 includes control circuitry that responds to the switch signal by directing to the drop generator head controlled current pulses for firing the drop generators as required. It will be appreciated that the control system can be configured in any of a number of ways and, most preferably, integrated with the housing 14 of the inhaler. Controller 24 includes appropriate processors and memory components. It will be appreciated that in some circumstances the circuitry that defines controller 24 may be incorporated into a real time clock circuit, and vice versa. Controller 24 also monitors the temperature of drop generator head 20 and specific nozzle areas within the ejector head. With respect to FIG. 2, the pressure sensor 34 may also be used to represent a temperature sensor 35. Suitable temperature sensors 35 include integrated circuit temperature sensors such as thermistors and resistors, thin film metals, metal oxide semiconductor temperature sensors, CMOS or MOS transistors, bipolar transistors, circuits defining a Wheatstone bridge, and others. Depending upon the specific usage, more than one temperature sensor may be utilized. Although not shown, MDI 6 may include a display on housing 12 such as a liquid crystal display to alert the user to the status of the unit.

In the case where MDI 6 is configured for delivery of medication via inhalation by the patient, the drop generator or ejector head 20 is typically located near a mouthpiece 32. The ejector head 20 illustrated in FIG. 2 is thus located inwardly of the mouthpiece 32 to allow the aerosolized medication to mix with airflow as the patient inhales. It will be appreciated that the control system 26 and the arrangement and orientation of the drop generator head 20 in housing 12 provide for both precise metering of the amount of droplets ejected and of the amount of medication expelled, as well as the generation of suitably small droplets. That is, the expulsion of the medication from the medication reservoir 14 need not be accompanied with other mechanisms for reducing the volume of ejected liquid to suitably small droplets. The ejection route of medication aerosolized out of mouthpiece 32 is shown schematically with a series of arrows A in FIG. 2.

Various control mechanisms are used with metered dose inhalers, depending upon the nature and level of control that the prescribing physician wishes to provide to the patient. When such controls are included (none are shown in the illustrated embodiment) they may be activated or inactivated to suit the particular circumstances.

Control system 26 may also include a programming interface 44 connected to controller 24 and externally exposed at the rearward end of housing 12 (FIG. 2) for connection to a computer. Programming interface 44 includes conductor pads 46 (FIG. 3) that interconnect the interface through traces (as in a flex circuit) and buss interfaces to controller 24. The illustrated embodiment of programming interface 44 may be replaced, for example, with any suitable programming interface, including an infrared compliant data link, or other similar programming interface.

The details of operation of MDI 6 will now be explained with reference to the flow chart of FIG. 5. The operational mode 8 is depicted at the top of the flow chart and as detailed above is the mode during which medication may be delivered to the patient. In this mode, the pressure of the compliant chamber 16 and the ejector head 20 is as described above at a negative gauge pressure relative to the gauge pressure that is maintained in the medication reservoir 14. At all times when MDI 6 is powered, control system 26 monitors various operational aspects of the MDI to determine whether the unit is operating properly and to thereby determine if a maintenance mode is necessary. If according to this ongoing monitoring the control system determines that MDI 6 is operating within predetermined normal values for any given operational aspect that is being monitored, then the system remains in operational mode 8. If a monitored operational aspect indicates that the system is operating outside of a predetermined normal value or has exceed a predetermined critical value, then the control system 26 initiates a maintenance mode 10.

There are several operational aspects that system 26 may monitor to determine whether MDI 6 is operating normally, or abnormally as when a critical value has been reached, and thus whether a maintenance mode 10 should be initiated. As one exemplary embodiment of an operational aspect that may be monitored, the temperature of the resistors in ejector head 20 (step 50) may be monitored. If the temperature of the ejector head 20 (or monitored portions of it) is within a predetermined normal operation range (step 52), then control system 26 deems the unit to be operating properly and MDI 6 remains in the operational mode 8.

When the nozzles in ejector head 20 become clogged or if, for example, residues from medication dispensed through the ejector accumulate on the nozzles, or bubbles retained in the nozzles prevent the nozzles from operating properly, the temperature of the ejector head 20 rises. As noted above, the primary reason for an increase in temperature of ejector head 20 is the failure of liquid to escape the nozzles and hence carry heat away from the nozzles in the ejected fluid. If control system 26 senses that the temperature of the ejector head 20 (or portions of it) has risen above the predetermined normal operation range (step 52) and/or has reached a predetermined critical value, then control system 26 initiates maintenance mode 10.

As an alternative embodiment, control system 26 includes an information storage device or clock that accumulates information indicative of a time and/or number of drop ejections since a nozzle maintenance mode 10 last occurred. A maintenance mode 10 may be initiated based on the accumulated time and/or number of drop ejections or usage of the inhaler since the previous maintenance mode. For example, a predetermined critical value stored in control system 26 may be a number of nozzle firings (i.e., the number of times that the ejector head has been activated) since the last maintenance mode. If the number of nozzle firings exceeds the predetermined critical value, then a maintenance mode 10 is initiated. As still another example, an accumulated time since the last maintenance mode may be monitored as an operational aspect. Thus, a maintenance mode 10 may be initiated based on the time that has lapsed between the current time and the last previous maintenance mode.

Regardless of the particular type of operational aspect that controller 26 is monitoring, when a critical value has been detected by controller 26 a maintenance mode 10 is initiated and switch 30 is disabled so the patient cannot dispense medication. Control system 26 then opens valve 17 for a period of time sufficient to allow fluid to be flushed through the nozzles. As the fluid enters the compliant chamber 16 and ejector head 20 from the relatively higher pressure reservoir 14, the gauge pressure in the compliant chamber 16 and ejector head 20 rises and becomes positive. As fluid moves through the compliant chamber and the ejector head, air is pushed out ahead of the fluid and the combination of air moving through the nozzles and fluid flowing through them tends to clear any clogged nozzles or nozzles that have residue accumulated on them. The resistors in ejector head 20 are not fired during this positive purging mode.

Control system 26 then closes valve 17 and the compliant chamber 16 and ejector head 20 return to the normal pressure state—negative relative to the positive pressurized state of reservoir 14. At this time, control system 26 may optionally initiate a round of test firings (step 54) of the ejector head 20, while monitoring nozzle temperature, to determine if another positive pressure purge according to maintenance mode 10 is necessary. If after the test firings at step 54 the temperature of the ejector head is within the predetermined normal range, then no further purging is needed and then switch 30 is enabled. If the temperature after the test firings is outside of the predetermined normal range, further purging is necessary and another maintenance mode 10 is initiated. If this maintenance cycle is successful in restoring the ejector head to an operational condition (as determined by ejector head temperature), then switch 30 is reactivated. If repeated maintenance cycles fail to resolve the problem, the switch 30 remains disabled and the unit may require servicing since the proper dosage of medication may not be delivered if some nozzles are clogged.

Figure 6:
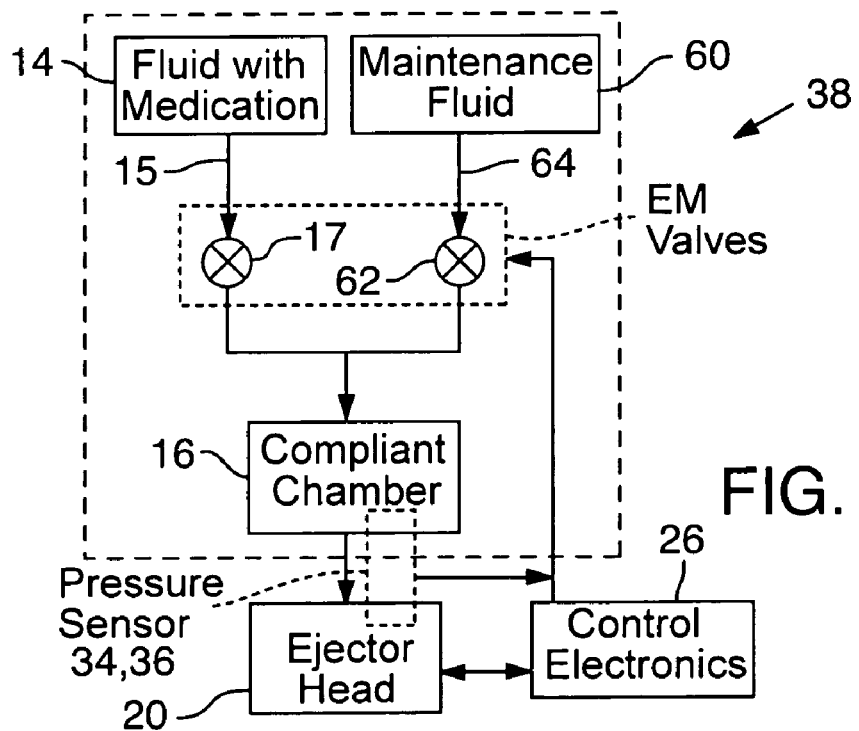
FIG. 6 is a schematic view of an alternative illustrated embodiment of the present invention similar to the embodiment shown in FIG. 5 but incorporating multiple supply containers.

Turning now to FIG. 6, an MDI 6 may be configured to use more than one supply reservoir 14. In the embodiment illustrated in FIG. 6 compliant chamber 16 and ejector head 20 are supplied fluid from two reservoir chambers, each of which is fluidly connected to the compliant chamber 16 with an independently controlled electromechanical valve. Thus, medication reservoir 14 is the same type of supply reservoir as described above with respect to the embodiment of FIGS. 2, 3 and 4. However, MDI 6 shown in FIG. 6 includes a second pressurized fluid reservoir identified as supply 60. In the embodiment illustrated, supply 60 is a supply of maintenance fluid. The maintenance fluid may include compounds intended to sterilize ejector head 20 during maintenance mode 10 operations. The maintenance fluid may include any number of appropriate cleaning compounds, including for example ethanol or sterilized water, etc.

Operation of the MDI shown in FIG. 6 is similar to the bimodal operation described above with respect to the single-pressurized reservoir 14 shown in FIG. 2. During operational mode 8, compliant chamber 16 and ejector head 20 are maintained at a relatively lower pressure than medication reservoir 14. Valve 17, which is under the control of the control electronics in control system 26 periodically opens valve 17 when in operational mode 8 to resupply medication to compliant chamber 16. When it is necessary to perform a pressurized maintenance mode 10, valve 17 is kept closed, the switch 30 (not shown in FIG. 6) is disabled, and valve 62 which is plumbed into conduit 64 exiting supply 60 is opened, thereby initiating positive pressurization of the compliant chamber 16 and ejector head 20. This positively pressurized flushing is identical to the maintenance mode 10 described above.

When control system 26 has determined that ejector head 20 is once again operational (by the temperature of ejector head 20 during test firings, as described above), valve 62 is closed so that the MDI 6 returns to operational mode 8. A supply of medication from medication reservoir 14 may then be provided to compliant chamber 16 by operation of valve 17, if needed.

An MDI 6 incorporating the nozzle maintenance system described herein may be used with more than two pressurized supply reservoirs as described with reference to FIG. 6. For example, in some cases an MDI will utilize two separate medication supply reservoirs—each filled with a different type of medication—and a separate maintenance supply reservoir. Each reservoir includes a valve that is independently controlled by the control electronics.

It will be appreciated that the volume of the compliant chamber 16 is preferably small—preferably less than 1 cm$^3$. The relatively low volume of compliant chamber 16 enables switching between operational mode 8 and maintenance mode 10 without flushing an undue amount of fluid (whether from a medication from reservoir 14 or a maintenance fluid supply 60) out of the system.

It will further be appreciated that those of ordinary skill in the art will recognize that modifications may be made to the systems and structures described herein without departing from the scope of the invention. For example, in the embodiments described above, fluid is maintained in a pressurized state in a supply reservoir and is supplied to the ejector head through and electronically activated valve. In one alternative embodiment, the supply reservoir could be maintained in a negative pressure state relative to the pressure in the compliant chamber, for example with a negative gauge pressure spring bag design used for the supply reservoir. When positive pressure is required to purge the ejector head, a mechanically operated mechanism may be used to engage the spring bag and to thereby force fluid into the fluid delivery system under positive pressure.

Finally, while the fluid supply reservoirs used in an MDI 6 are preferably replaceable, for instance, with a needle and septum type connection with the fluid conduits leading to the electromechanical valves, the MDI 6 may be fabricated as a disposable unit.

Having here described illustrated embodiments of the invention, it is anticipated that other modifications may be made thereto within the scope of the invention by those of ordinary skill in the art. It will thus be appreciated and understood that the spirit and scope of the invention is not limited to those embodiments, but extend to the various modifications and equivalents as defined in the appended claims.

The invention claimed is:

1. A medication delivery apparatus, comprising:
a first pressurized supply of fluid in a reservoir;
a fluid conduit from the supply to an ejector head including at least one selectively disabled resistor;
a valve operatively positioned in the fluid conduit between the supply and the ejector head;
a programmable controller;
wherein the reservoir, the fluid conduit, and the ejector head form a fluidically connected fluid delivery unit controlled by the programmable controller;
a first operational mode controlled by the controller, wherein, in the first operational mode of the fluid delivery unit, the ejector head is operable to deliver fluid from the reservoir through the ejector head, the fluid in the ejector head and the fluid conduit being at a lower pressure relative to the fluid in the reservoir; and
a second maintenance mode controlled by the controller, wherein, in the second maintenance mode of the fluid delivery unit, the at least one resistor of the ejector head is disabled and the valve is opened to create positive pressure throughout the reservoir, the fluid conduit and the ejector head; the positive pressure purging out all remaining fluid from the fluid delivery unit by way of the disabled ejector head, and the positive pressure for the second maintenance mode being generated by opening the valve and disabling the at least one selectively disabled resistor.

2. The apparatus according to claim 1 including a pressure regulation apparatus in the reservoir to maintain the supply of fluid in a pressurized state.

3. The apparatus according to claim 1 including sensor means for monitoring an operational aspect of the ejector head.

4. The apparatus according to claim 3 where the sensor means comprises a temperature sensor capable of measuring the temperature of a portion of the ejector head.

5. The apparatus according to claim 3 wherein the sensor means comprises a counter for counting the number of times that the ejector head has been activated.

6. The apparatus according to claim 3 wherein the sensor means comprises a clock for measuring the time interval from a prior maintenance mode.

7. The apparatus according to claim 4 wherein the temperature sensor is under the control of the programmable controller.

8. A medication delivery apparatus, comprising:
a first pressurized supply of fluid in a reservoir;
a fluid conduit from the supply to an ejector head including at least one selectively disabled resistor;
a first valve positioned in the fluid conduit between the supply and the ejector head;
a programmable controller capable of operating the delivery apparatus in a first operational mode wherein the ejector head is operable to deliver fluid from the supply through the ejector head, and in a second maintenance mode wherein the at least one selectively disabled resistor of the ejector head is disabled and fluid is purged through the ejector head;
a second pressurized supply of fluid in a reservoir;
a second fluid conduit from the second pressurized supply of fluid to the ejector head; and
a second valve positioned in the second fluid conduit.

9. The apparatus according to claim 8 wherein the fluid in the first pressurized supply of fluid comprises a medication.

10. The apparatus according to claim 9 wherein the fluid in the second pressurized supply of fluid comprises a maintenance fluid.

11. An inhalation system, comprising:
an ejector head including at least one selectively disabled resistor;
a pressurizable supply of fluid in a reservoir, the reservoir having a pressure regulation apparatus that supplies fluid to the ejector head at a controllable pressure;
a fluid conduit from the reservoir to the ejector head
a valve in the fluid conduit positioned between the reservoir and the ejector head; and
a control system;
wherein the reservoir, the fluid conduit, and the ejector head form a fluidically connected fluid delivery unit controlled by the control system, the control system being configured to control the fluid supply system in two different modes including (a) an operating mode wherein the fluid is supplied to the ejector head with an operational pressure such that the fluid in the ejector head and the fluid conduit are at a lower pressure relative to the fluid in the reservoir and (b) an ejector head purge mode wherein the at least one selectively disabled resistor of the ejector head is disabled, and the valve is opened to create positive pressure throughout the reservoir, the fluid conduit and the ejector head, the positive pressure purging out all remaining fluid from the fluid delivery unit by way of the disabled ejector head, the positive pressure for the ejector head purge mode being generated by opening the valve and disabling the at least one selectively disabled resistor.

12. The inhalation system according to claim 11 wherein the ejector head includes thermal drop generators.

13. The inhalation system according to claim 11 wherein the fluid at the operational pressure is at a negative gauge pressure.

14. The inhalation system according to claim 13 wherein the fluid at the purge pressure is at a positive gauge pressure.

15. An inhalation system, comprising:
an ejector head including at least one selectively disabled resistor;
a fluid supply system having a pressure regulation apparatus that supplies fluid to the ejector head at a controllable pressure; and
a control system configured to control the fluid supply system in two different modes including: (a) an operating mode wherein the fluid is supplied to the ejector head with an operational pressure; and (b) an ejector head purge mode wherein the at least one selectively disabled resistor is disabled and a valve positioned between the ejector head and fluid supply system is opened, and the fluid supply pressure is at a purge pressure that is different from the operational pressure;

wherein the fluid supply system includes first and second fluids, and wherein the control system is configured for supplying the first fluid to the ejector head in the operating mode and the second fluid to the ejector head in the ejector head purge mode.

16. The inhalation system according to claim 15 in which the first fluid comprises a medication and the second fluid comprises a maintenance fluid.

* * * * *